(12) United States Patent
Doubler et al.

(10) Patent No.: US 10,258,385 B1
(45) Date of Patent: Apr. 16, 2019

(54) BOTTOM LOADING POLYAXIAL BALL AND SOCKET FASTENER WITH BLOCKING RING WITH NOTCHED SPLIT RING

(71) Applicant: Spinal LLC, Palm Beach Gardens, FL (US)

(72) Inventors: Robert L. Doubler, Monroe, MI (US); John E. Hammill, Sr., Maumee, OH (US)

(73) Assignee: Spinal LLC, Palm Beach Gardens, FL (US)

( * ) Notice: Subject to any disclaimer, the term of this patent is extended or adjusted under 35 U.S.C. 154(b) by 0 days.

(21) Appl. No.: 16/040,809

(22) Filed: Jul. 20, 2018

Related U.S. Application Data

(63) Continuation-in-part of application No. 15/839,179, filed on Dec. 12, 2017.

(51) Int. Cl.
*A61B 17/70* (2006.01)

(52) U.S. Cl.
CPC ...... *A61B 17/7037* (2013.01); *A61B 17/7032* (2013.01)

(58) Field of Classification Search
CPC ........ A61B 17/7001; A61B 17/7032–17/7046; A61B 17/8605–17/866
See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,483,334 A | 11/1984 | Murray |
| 4,693,240 A | 9/1987 | Evans |
| 4,708,510 A | 11/1987 | McConnell et al. |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,129,900 A | 7/1992 | Asher et al. |
| 5,133,717 A | 7/1992 | Chopin |
| 5,501,684 A | 3/1996 | Schlapfer et al. |
| 5,549,608 A | 8/1996 | Errico et al. |
| 5,569,247 A | 10/1996 | Morrison |
| 5,591,166 A | 1/1997 | Bernhardt et al. |
| 5,716,357 A | 2/1998 | Rogozinski |
| 5,800,435 A | 9/1998 | Errico et al. |
| 6,485,491 B1 | 11/2002 | Farris et al. |
| 6,565,567 B1 | 5/2003 | Haider |
| 6,672,788 B2 | 1/2004 | Hathaway |

(Continued)

*Primary Examiner* — Ellen C Hammond
*Assistant Examiner* — Tessa Matthews
(74) *Attorney, Agent, or Firm* — McHale & Slavin, P.A.

(57) ABSTRACT

The bottom loading fastening system that consists of the polyaxial ball and socket joint used in conjunction with a bone screw. The system allows attachment to a bone screw using a retaining ring with a blocker ring to assure proper ring positioning. The retaining ring having a continuous inner surface wall and an outer wall having a notch. Upon installation the retainer wall is expanded causing a break at the notch producing an audible and tactile indication that the sufficient force has been applied to set the retainer and blocker rings locking the bone screw to a U-shaped connecting assembly.

7 Claims, 10 Drawing Sheets

(56) References Cited

U.S. PATENT DOCUMENTS

| | | |
|---|---|---|
| 6,716,214 B1 | 4/2004 | Jackson |
| 7,066,937 B2 | 6/2006 | Shluzas |
| 7,445,627 B2 | 11/2008 | Hawkes et al. |
| 7,947,065 B2 | 5/2011 | Hammill, Sr. et al. |
| 8,075,603 B2 | 12/2011 | Hammill, Sr. et al. |
| 8,465,065 B2 | 6/2013 | Browne et al. |
| 8,556,938 B2 * | 10/2013 | Jackson ............ A61B 17/7008 |
| | | 606/269 |
| 9,615,858 B2 | 4/2017 | Doubler et al. |
| 9,707,013 B2 * | 7/2017 | Rezach ............ A61B 17/7037 |
| 2003/0118395 A1 | 6/2003 | Abels et al. |
| 2006/0149240 A1 | 7/2006 | Jackson |
| 2006/0155277 A1 | 7/2006 | Metz-Stavenhagen |
| 2006/0235392 A1 | 10/2006 | Hammer et al. |
| 2006/0241599 A1 | 10/2006 | Konieczynski et al. |
| 2008/0015579 A1 * | 1/2008 | Whipple ............ A61B 17/7037 |
| | | 606/250 |
| 2008/0177322 A1 | 7/2008 | Davis et al. |
| 2008/0269809 A1 | 10/2008 | Garamszegi |
| 2014/0012337 A1 | 1/2014 | Biedermann et al. |
| 2015/0320465 A1 * | 11/2015 | Butler ............... A61B 17/8605 |
| | | 606/308 |
| 2016/0331412 A1 * | 11/2016 | Biedermann ...... A61B 17/7037 |
| 2016/0331413 A1 * | 11/2016 | Daniels ............. A61B 17/7032 |
| 2017/0333085 A1 * | 11/2017 | Jackson .............. A61B 17/702 |

\* cited by examiner

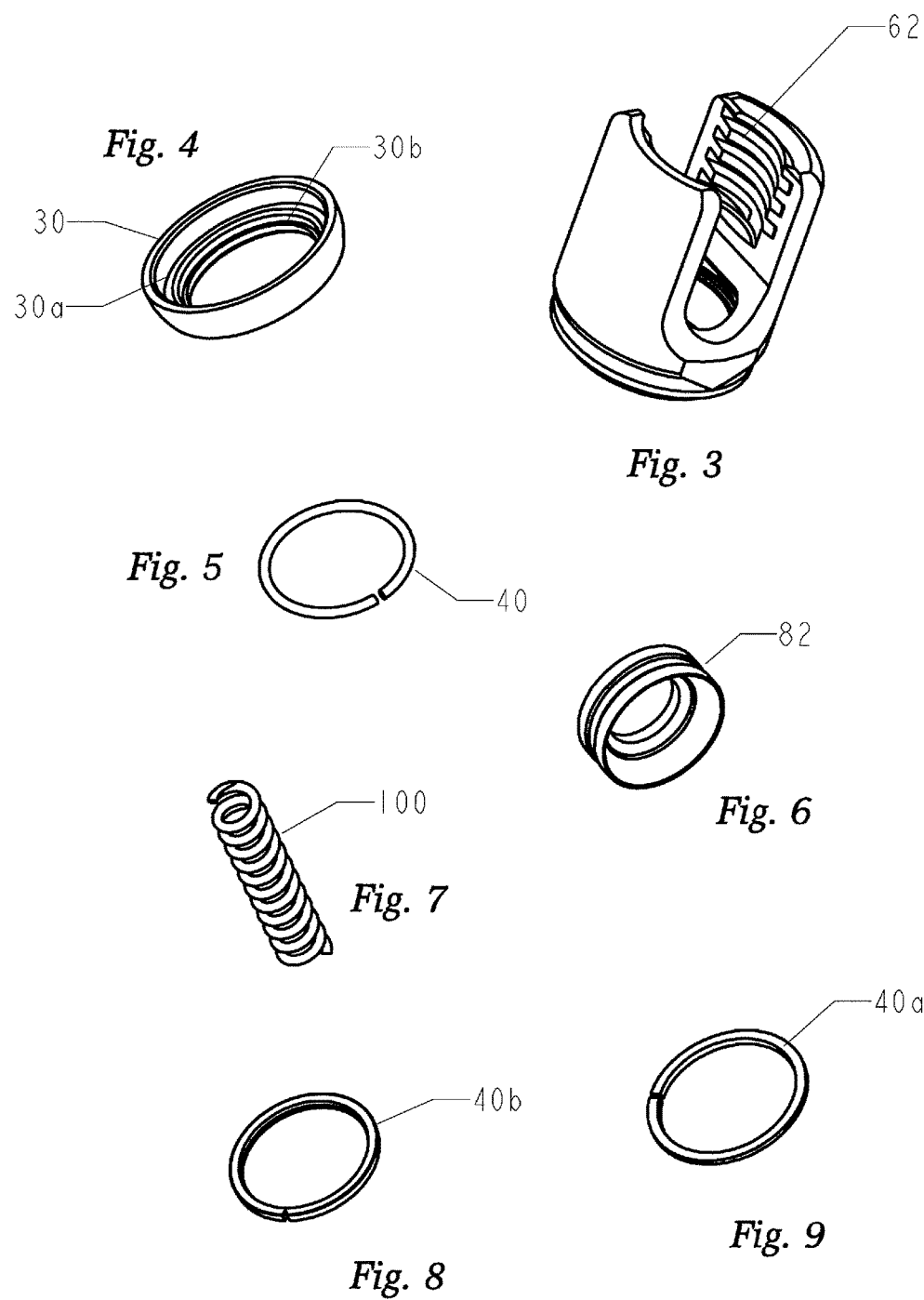

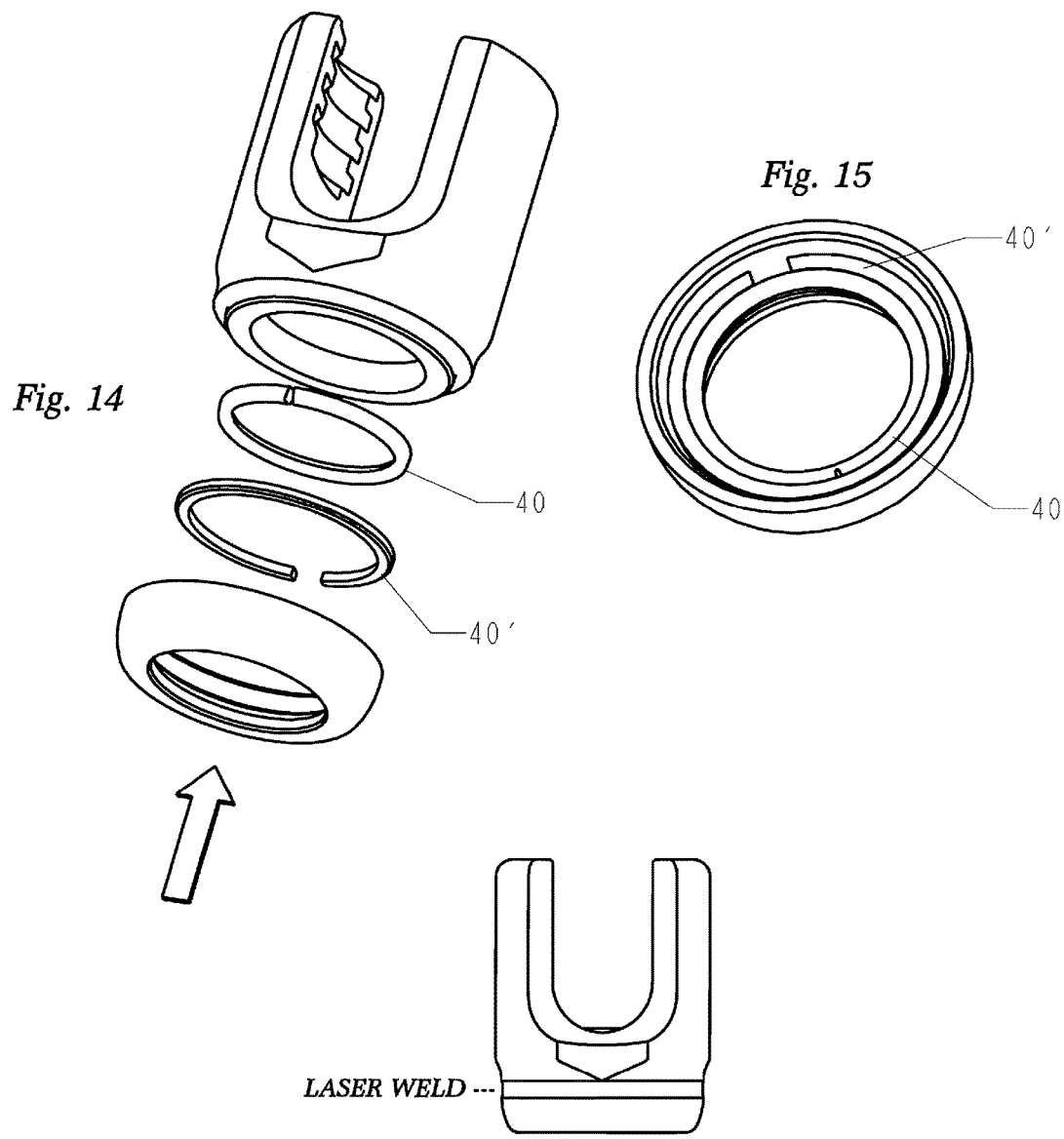

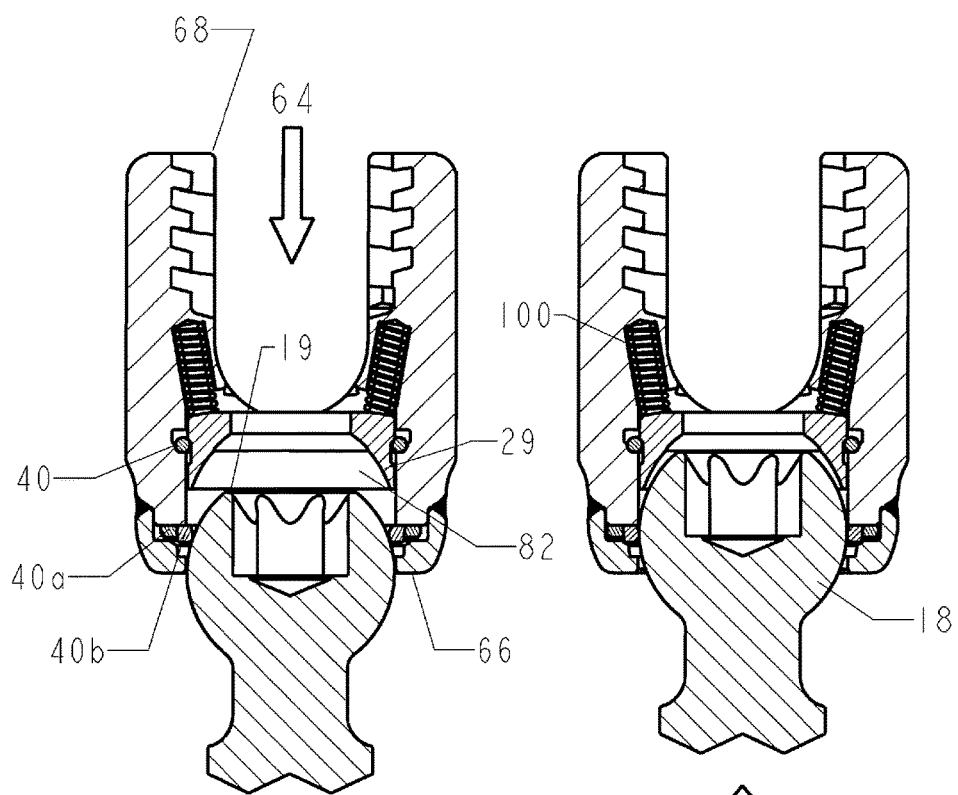
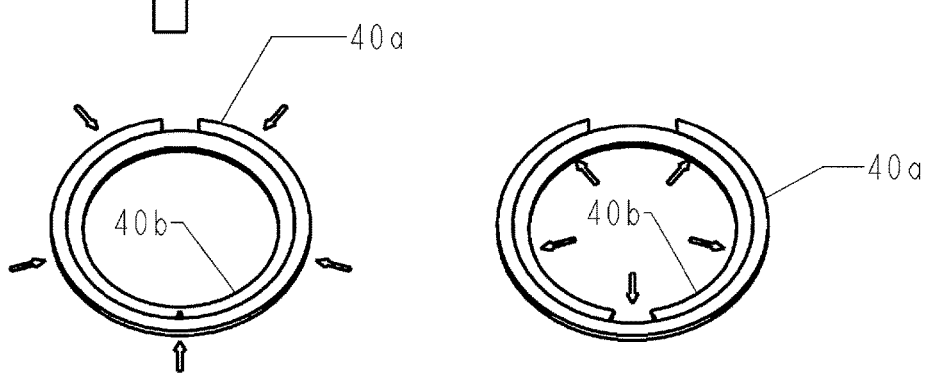
Fig. 17    Fig. 19
Fig. 18    Fig. 20

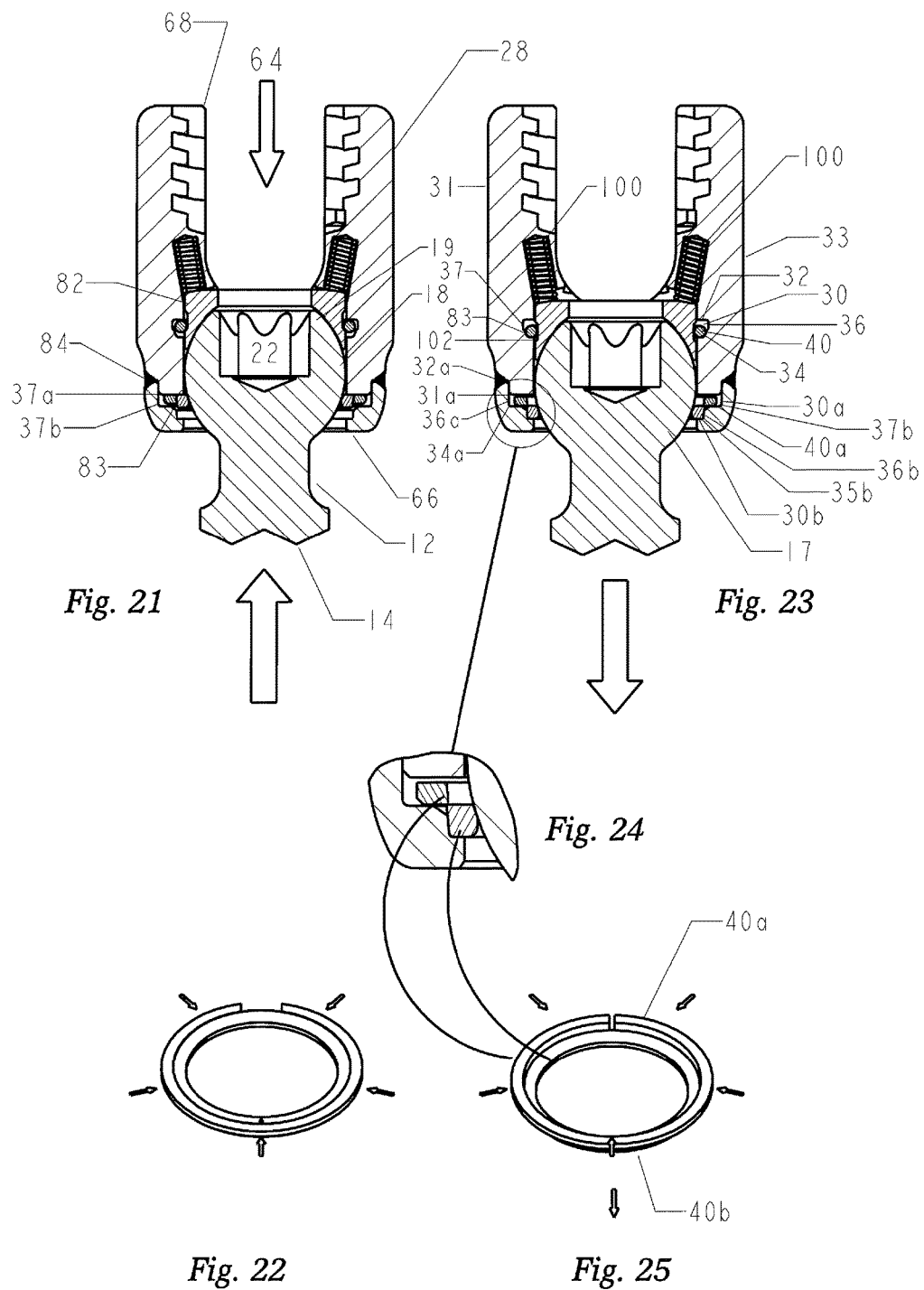

BOTTOM LOADING POLYAXIAL BALL AND SOCKET FASTENER WITH BLOCKING RING WITH NOTCHED SPLIT RING

PRIORITY CLAIM

In accordance with 37 C.F.R. 1.76, a claim of priority is included in an Application Data Sheet filed concurrently herewith. Accordingly, the present invention claims priority as a continuation-in-part of U.S. patent application Ser. No. 15/839,179 entitled SPRING CLIP BOTTOM LOADING POLYAXIAL BALL AND SOCKET FASTENER filed Dec. 12, 2017 incorporated herein by reference.

FIELD OF THE INVENTION

This invention is directed to the field of ball and socket fasteners, and in particular to a polyaxial ball and socket fastener having a notched split ring adapted for use as a spinal implant.

BACKGROUND OF THE INVENTION

There are numerous ball and socket fasteners, however, when the application is applied to a particular product, the ball and socket must meet minimum specifications in order to be effective. For instance, in the field of spinal pathologies, the development of spinal fixation devices represents a major medical breakthrough. Surgically implanted fixation systems are commonly used to correct a variety of back structure problems, including those which occur as a result of trauma or improper development during growth. A commonly applied fixation system includes the use of one or more stabilizing rods aligned in a desired orientation with respect to a patient's spine. Anchoring screws are inserted into the patient's spinal bones, and a series of connectors are used to rigidly link the rods and anchors.

A variety of designs exist, with each design addressing various aspects of the difficulties that arise when one re-shapes an individual's spine to follow a preferred curvature. Known spinal implant systems often correct one set of problems only to create new ones.

Common to all spinal implant systems is the necessity for proper anchoring to the bone so as to provide support for the aforementioned components. While bone screws are commonly used for anchoring, the use of a polyaxial design has proven very effective in allowing a surgeon the flexibility to secure an installation with minimal strain on the individual.

For this and other reasons, screws located in bone structure typically use a polyaxial base and a specially designed connector member for attachment to a component such as an alignment rod. A problem with the current technology is that bone structure cannot be determined until the patient's bone is exposed. This problem requires a large inventory of various sized implants to be on hand during every surgery. The surgeon must search through the inventory to assemble a combination based on his prediction of what will be required. Even if an implant combination is predicted, the anchoring screw may still require angular insertion due to muscle structure or nerve locations. Any movement of muscle and other tissue increases the difficulty of the operation and can be a major trauma to the patient. Still yet, bone condition may require oversize threads to achieve a suitable purchase to the bone. As a consequence, the surgeon must either maintain a large inventory of anchoring devices, or have a vendor standing by with a large inventory of anchoring devices that will hopefully meet the individual requirements.

One of the problems with a polyaxial pedicle screw is the lack of a stabilized angular placement position during installation. Once a polyaxial pedicle screw is inserted into the bone, the connector component portion has yet to receive a connecting rod leaving the connector assembly to flop over making it difficult for the Surgeon to grasp while in the midst of surgery. This problem is compounded by the need to align multiple component heads for receipt of a connecting rod.

U.S. Pat. No. 7,066,937 discloses an apparatus including a housing having a first passage configured to receive a longitudinal member and a second passage with an axis transverse to the first passage; a fastener extending through an opening in the housing and being moveable relative to the housing; the second passage of the housing having an indentation, the indentation including an axially extending surface at least partially defining the second passage and an upper surface extending transverse to the axially extending surface, a spacer received in the second passage of the housing, the spacer having a radial surface below the upper surface of the indentation; and a member contacting the upper surface of the indentation and the radial surface of the spacer that applies an axial force to the spacer to prevent relative movement between the fastener and the housing and holding the fastener in any one of a plurality of angular positions relative to the housing.

U.S. Pat. Nos. 7,947,065; 8,075,603 and 8,465,065 disclose a polyaxial ball and socket joint used in conjunction with a bone screw having threads on one end for use in anchoring to the spine and a spherical connector on the other end operating as a pivot point about which a connecting assembly moves in a polyaxial fashion. A substantially U-shaped connecting assembly has a lower receptacle that operates as a socket for housing an upper retainer ring and a lower split retaining ring. The socket is receptive to the spherical connector which is inserted through the lower split retainer ring causing a momentary displacement thereof which allows for the positioning of the spherical connector between the upper and lower retainer rings.

U.S. Pat. No. 6,485,491 discloses a multi-axial bone anchor assembly that includes a saddle member, a bone anchoring member and a washer. The saddle has a channel that receives a rod. A snap ring secures the washer in the saddle member. The snap ring engages a snap ring recess. The disclosed structure would not prevent relative movement between a fastener and housing and would not hold a longitudinal axis of the fastener in any one of a plurality of desired angular positions relative to a longitudinal of a passage in the housing when a rod, longitudinal member, is disengaged from a spacer. The patent does not teach an arrangement where a spacer necessarily engages a fastener when a rod, longitudinal member, is so disengaged.

A conventional polyaxial bone screw typically consists of a single shaft with a coarse thread at one end for threading into the bone. A spherical ball is positioned at an opposite end for coupling to a connecting member. For example, a number of patents exist for bone screw anchoring assemblies that include a U-shaped connector element which acts as a saddle for attachment to an alignment rod. U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion designed for threadingly engaging a semi-spherical cup for use with a specially designed alignment rod. The alignment rod includes spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are designed with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employ connectors that join the support rods and anchoring screws. The connectors eliminate unwanted relative motion between the rod and the screws, thereby maintaining the patient's spine in a corrected orientation.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths.

U.S. Pat. No. 7,445,627 discloses a fastener and a bone fixation assembly for internal fixation of vertebral bodies. According to one exemplary embodiment, a tulip assembly is employed, the tulip assembly includes a non-circular surface disposed on its outer surface. A fastener is coupled to the tulip assembly and positionable to retain the tulip assembly on the head of a screw. A cap having an outer surface and a plurality of inner protrusions mateably connects to the non-circular surface on the tulip body to compress the tulip assembly to secure a rod.

U.S. Publication No. 2008/0177322 discloses a spinal stabilization system that includes bone fastener assemblies that are coupled to vertebrae. Each bone fastener assembly includes a bone fastener and a collar. The bone fastener has a head portion having at least a first cross-sectional shape in a first plane, and a second cross-sectional shape in a second plane. The collar has a circular opening in the bottom, with a relief extending from the circular opening. The second cross-sectional shape of the bone fastener is keyed to the opening to permit insertion of the bone fastener into the collar assembly from the bottom. After insertion, the bone fastener is rotated to prohibit removal of the bone fastener from the collar. The collar can then be rotated and/or angulated relative to the bone fastener. An elongated member can be positioned in the collar and a closure member is then used to secure the elongated member to the collar.

U.S. Publication No. 2006/0241599 discloses a polyaxial fixation device having a shank with a spherical head formed on a proximal end thereof, and a receiver member having an axial passage formed therein that is adapted to polyaxially seat the spherical head of the shank. The polyaxial bone screw further includes an engagement member that is adapted to provide sufficient friction between the spherical head and the receiver member to enable the shank to be maintained in a desired angular orientation before locking the spherical head within the receiver member.

U.S. Publication No. 2006/0235392 discloses a system for connecting a fastener element (e.g., a pedicle screw) relative to a rod for the purposes of vertebral fixation. The system may permit multi-axial movement between the fastener element and the rod. Further, the system may permit the angular relationship between the fastener element and the rod to be held in a desired orientation.

U.S. Publication No. 2006/0155277 discloses an anchoring element for securing a rod on a vertebra, that comprises a retaining means for receiving the rod, a safety element placed on the retaining means, a securing element which can be placed on the body of the vertebra, and a clamping device which is arranged between the retaining means and the securing element. The clamping device includes a ring-shaped mount, a partially conical-segment shaped bearing and an intermediate element which is embedded in the mount and which engages the bearing, whereby the mounting is moveable in a removed state in relation to the bearing, whereas the mount is maintained in a clamped state on the bearing by means of the intermediate element. The mount is rigidly connected to the retaining means and the bearing is rigidly connected to the securing element.

U.S. Publication No. 2006/0149240 discloses a polyaxial bone screw assembly that includes a threaded shank body having an upper capture structure, a head and a multi-piece retainer, articulation structure. The geometry of the retainer structure pieces correspond and cooperate with the external geometry of the capture structure to frictionally envelope the retainer structure between the capture structure and an internal surface defining a cavity of the head. The head has a U-shaped cradle defining a channel for receiving a spinal fixation or stabilization longitudinal connecting member. The head channel communicates with the cavity and further with a restrictive opening that receives retainer pieces and the capture structure into the head but prevents passage of frictionally engaged retainer and capture structures out of the head. The retainer structure includes a substantially spherical surface that mates with the internal surface of the head, providing a ball joint, enabling the head to be disposed at an angle relative to the shank body.

U.S. Pat. No. 6,716,214 discloses a polyaxial bone screw having a bone implantable shank, a head and a retaining ring. The retaining ring includes an outer partial hemispherical surface and an inner bore with radially extending channels and partial capture recesses. The shank includes a bone implantable body with an external helical wound thread and an upwardly extending capture structure. The capture structure includes at least one spline which extends radially outward and has a wedged surface that faces radially outward therefrom. The capture structure operably passes through a central bore of the retaining ring while the spline passes through a suitably shaped channel so that the spline becomes positioned above the head, at which time the shank is rotated appropriately and the shank is drawn back downwardly so that the spline engages and seats in the capture recess. The head includes an internal cavity having a spherical shaped surface that mates with the ring surface and has a lower restrictive neck that prevents passage of the ring once the ring is seated in the cavity.

U.S. Pat. No. 6,565,567 discloses a pedicle screw assembly for use with a rod for the immobilization of bone segments. The assembly is comprised of a screw, a polyaxial housing for receiving the screw, a washer, a set screw, and a cup-shaped cap. The lower portion of the housing terminates in a reduced cross-sectional area, which engages the bottom of the screw head. When the screw is placed inside the polyaxial housing and the screw is secured into the bone, the polyaxial housing is pivotable with three degrees of freedom. The housing includes a top portion with a pair of upstanding internally threaded posts. A washer is inserted between the head of the screw and the rod. A cap, having a bottom, with a pair of posts accommodating openings and a lateral cross connector, is placed over the posts so that the cross connector engages the rod. The cross connector and washer have concave generally semi-cylindrical rod engaging surfaces to prevent the rod from rotating or sliding within the housing once the set screw is tightened. A set screw is threaded into the housing posts to secure the rod within the housing. The washer has a roughened lower surface which, in conjunction with the reduced cross-sectional area at the bottom of the housing, securely clamps and locks the housing to the screw head when the set screw is tightened.

U.S. Pat. No. 5,501,684 discloses an osteosynthetic fixation device which consists of a fixation element which has a conical head section and an anchoring element abutting it which is for attachment into the bone. The fixation device also consists of a spherically formed, layered, slotted clamping piece which has a conical borehole for installation of the conical head section, and which is meant for locking within a connecting piece equipped with a spherically shaped layered borehole. Fixation piece has an axially arrayed tension element, permitting axial displacement and wedging of conical head section in the borehole that corresponds with it. The fixation device is appropriate for use as a plate/screw system, an internal or external fixator, and in particular for spinal column fixation.

U.S. Pat. No. 4,693,240 discloses a bone pin clamp for external fracture fixation. The apparatus comprises rotation, slide and housing elements nested one within the next, each such element having an aperture to receive a pin there through, and the rotation and slide elements respectively affording pin adjustment in azimuth and zenith, and in height, relative to the housing element. A locking mechanism including a common actuator member is operable simultaneously to lock the pin and rotation and slide elements in the housing element. In a preferred form, the housing element serves as a cylinder with the slide element as a keyed piston therein, and the rotation element is a disc located between a screw and annular thrust members engaged in the piston, the piston and disc being split respectively to lock by expansion and compaction under screw action towards the thrust members.

U.S. Pat. No. 4,483,334 discloses an external fixation device for holding bone segments in known relation to each other. The device includes a pair of bone clamp assemblies each secured to bone pins extending from the bone segments, a bridge extending between the pin clamp assemblies, and a specialized high friction universal assembly connecting the bridge to each of the pin clamp assemblies.

U.S. Pat. No. 4,273,116 discloses an external fixation device for reducing fractures and realigning bones that includes sliding universal articulated couplings for enabling easy adjustment and subsequent locking of connections between Steinmann pins and tubular tie-rods. The couplings each include a split, spherical adapter sleeve which is embraced by the matching inner surface of an open ring portion of a coupling locking clamp having clamp lugs tightenable against a block by means of a nut-and-bolt assembly. Further nut-and-bolt assemblies are disposed in elongated slots in the blocks and cooperate with associated clamping members to clamp the Steinmann pins to the blocks after adjustment in two orthogonal directions and optional resilient bending of the pins.

U.S. Pat. No. 6,672,788 discloses a ball and socket joint incorporating a detent mechanism that provides positive biasing toward a desired position. The ball and socket joint can be used in flexible supports that hold and support items such as lamps, tools and faucets. The detent mechanism comprises two corresponding parts, one in the ball portion and the second in the socket portion of the joint. The first detent part is a protrusion of some type and the second detent part is a groove or indentation that is adapted to accept and engage the protrusion. If the ball contains the detent protrusion, then the socket contains the detent indentation. And conversely, if the socket contains the detent protrusion, then the ball contains the detent indentation. The detent tensioning force can be provided by a spring or a spring band, the characteristics of the material from which the joint is made, or by some other similar tensioning device.

U.S. Publication No. 2003/0118395 discloses a ball and socket joint, which has a housing, a ball pivot mounted pivotably in the housing, and a sealing bellows, which is fastened to the housing and is mounted on the ball pivot slidably via a sealing ring provided with two legs. A first leg of the two legs is in contact with the ball pivot under tension and the second leg meshes with the wall of the sealing bellows. The second leg is, furthermore, fastened in an anchoring ring arranged at least partially in the wall of the sealing bellows.

U.S. Pat. No. 4,708,510 discloses a ball joint coupling assembly that permits universal movement and positioning of an object with respect to a vertical support shaft. Quick release/lock action is provided by a ball joint assembly having a housing in which a ball and piston are movably coupled. The ball is captured between annular jaw portions of the housing and piston, with locking action being provided by gripping engagement of the piston jaw portion and the housing jaw portion. The ball member is gripped in line-contact, compressive engagement by the annular edges of the piston jaw and housing jaw on opposite sides of the ball. The piston is constrained for axial movement within the housing with locking engagement and release being effected by rotation of a threaded actuator shaft.

U.S. Pat. No. 3,433,510 discloses a swivel structure for rigidly joining first and second parts together. A first member is connected to the first part and a second member is connected to the second part. An intermediate hollow member interconnects the first and second members together. An enlarged outer end portion is provided on the first member and includes a plurality of locking means thereon. Means are provided on the second member for engaging one of the locking means. Means are provided for threadably joining the hollow member and the second member together. A slot is provided in the hollow member and includes an enlarged entrance which passes the enlarged outer end portion and which also includes a restricted opening opposite the threaded joining of the hollow member and the second member together. The portion surrounding the restricted opening opposes the forces imparted against the outer end portion as the second member is threadably joined to the hollow portion and bears against the outer end portion.

U.S. Patent Publication No. 2008/0269809 discloses a bottom loading pedicle screw assembly. The device includes a pedicle screw and a connector member. The pedicle screw includes a threaded lower portion while the upper portion includes a groove sized to accept a clip member. The clip member includes a spherical outer surface. In operation the clip is placed within the groove and the assembly is pressed through the opening in the bottom of the connector member. While the device is bottom loading, the device will separate when the pedicle screw is aligned with the connector member. The construction of the clip member allows the clip to collapse sufficiently to pass back through the opening when the screw is positioned in alignment with the connector, requiring the connection to bone be placed at an angle with respect to the connector for proper operation.

SUMMARY

Briefly, the present invention is a bottom loading polyaxial ball and socket joint capable of snap together assembly. Disclosed is an exemplary embodiment of the ball and socket fastening system adapted for use in a spinal fixation system for reshaping the spine of a patient. The fixation system includes the polyaxial ball having a bone screw extending outwardly therefrom for use in anchoring to the spine and a connector member that includes a socket constructed and arranged to accept the polyaxial ball. Upon placement of the bone screw, the connector member can be attached to the bone screw. In the disclosed embodiment, the connector member is illustrated as a U-shaped connector member having at least one groove at the base of the connector. The groove operates as a socket for housing a split ring retainer and a blocker split ring. The U-shaped connector further comprises at least one cavity or borehole which extends upwards from the junction or interface between the U-shaped connector and anchor cap into the body of the U-shaped connector. The boreholes or cavities can be at an angle less than or equal to 90 degrees with respect to the interface between the anchor cap and U-shaped connector. The interface between the anchor cap and U-shaped assembly is in general, a planar surface. Within the socket is an anchor cap for receipt of the spherical ball connector. The anchor cap comprises a planar surface and at least one compressible or non-compressible member which fit into the one or more cavities or boreholes of the U-shaped connector.

The socket is receptive to the spherical connector which is inserted through an aperture in the bottom of the connector assembly where the spherical polyaxial ball contacts the split retainer ring and blocker causing a momentary displacement thereof, allowing the ball to pass through the ring positioning.

Once the ball has past through the ring positioning, the blocker ring substantially encapsulates the retainer ring preventing the retainer ring from reopening. The blocker ring essentially removes the space between the outer diameter of the retainer ring and the inner diameter of the spherical connector.

A set screw or nut can then be utilized to press a connecting rod into contact with the ball while simultaneously causing the lower portion of the spherical ball connector to wedge against the inner surface of the connector member immobilizing the connection.

During surgery a surgeon can determine the most advantageous bone screw or other type of bone connection to match the connecting assembly. After inserting the bone screw into the desired location, the bone connector is then coupled to the connector assembly by inserting or snapping the spherical connector into the socket of the connecting assembly. In operation, the spherical connector is pushed past the retainer rings whereby the rings snap past the largest diameter of the connector to prohibit removal of the connector while still allowing polyaxial movement between the spherical ball and the connector member. In the preferred embodiment, the retainer rings are resiliently biased against a lower and an upper surface of the spherical connector and engage the spherical connector so as to keep the U-shaped connector member in position during installation. The compressible or non-compressible members of the anchor cap provide further stability so as to keep the U-shaped connector member in position during installation. A surgeon can easily move the spherical connector member into a preferred position and the resilient split ring will keep sufficient force between the lower surface of the spherical connector and the groove so as to maintain the spherical connector in a selected position relative to the connector assembly. This facilitates the installation of the rod as the U-shaped connector not only can be rotated into a position for proper placement of the connecting rod but the proper angle of the U-shaped connector can also be maintained while allowing the surgeon to align additional screws for ease of rod placement.

Because of the flexibility and resilience of the retaining rings, the mating parts do not require fine tolerances and are economical to manufacture. The system is modular, employing a collection of anchoring assemblies that are linked, via various connectors, to strategically-arranged stabilizing rods.

The connector members are rigid structures adapted to link an associated anchoring assembly with one of the stabilizing rods. The stabilizing rods may be rigid or dynamic members shaped to form a spine-curvature-correcting and/or immobilizing path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

Accordingly, it is an objective of the present invention to teach the use of a bottom loading polyaxial ball and socket fastener for use in a spinal stabilization system utilizing a retainer ring that allows insertion of a pedicle screw ball and is then stopped from reopening by a split ring blocker.

Another objective of the invention is to disclose the use of a polyaxial ball and socket system that is capable of securing various anchors to various connector members so as to reduce the amount of inventory required to meet a particular installation.

It is another objective of the present invention to provide a polyaxial bone screw assembly for a spinal fixation system that permits component adjustment during installation, thereby enabling satisfactory correction of a wide variety of spinal deformities.

It is an additional objective of the present invention to provide a bone screw assembly that includes a split ring locking mechanism that is simple, strong and reliable. Wherein a blocker ring holds a retainer ring in place by interference fit between the outer diameter of the retainer ring and inner diameter of the blocker ring.

It is yet another objective of the present invention to provide a blocker ring having a circular shape that approaches 360 degrees of coverage around the retainer ring.

Another objective of the invention is to teach the use of a retainer ring formed from a 360 degree ring that becomes split when the spherical head of a screw is forced through the retainer ring during assembly. The retainer ring having a notched to provide a tactile feel when the notch is propagated into a split of the retainer ring.

Another objective of the invention to provide a spinal fixation system that has an audible sound as well as a tactile feel when the spherical ball causes the retainer ring to split.

Still another objective of the invention to provide a spinal fixation system that has a tactile feel wherein the retainer clip snaps into position to indicate proper installation.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 3 is a perspective view of the U-shaped connector;
FIG. 4 is a perspective view of the annulus formed at the distal end of the U-shaped connector and grooves therein for receipt of a retaining ring;
FIG. 5 is a perspective view of a split-ring;
FIG. 6 is a perspective view of an anchor cap;
FIG. 7 is a perspective view of a compressible member;
FIG. 8 is a perspective view of a split ring constructed and arranged to fit into a retention ring;
FIG. 9 is a perspective view of a retention ring constructed and arranged to receive a split ring of FIG. 8;
FIG. 14 is a perspective view of the various sections of the U-shaped connector;
FIG. 15 is a perspective view of a split ring and a retention ring disposed in a ring groove of the annulus formed at the distal end of the U-shaped connector;
FIG. 16 is a plane view of the U-shaped connector;
FIG. 17 is a cross-sectional view of the ball and socket fastener with the anchoring member illustrating the initial step of the insertion of a bone screw into the U-shaped connector member;
FIG. 18 is a perspective view of the positioning of the split ring and retaining ring of the assembly in FIG. 17;
FIG. 19 is a cross sectional view of the ball and socket fastener with the anchoring member illustrating a step in the capturing of the head of the bone screw;
FIG. 20 is a perspective view of the positioning of the split ring and retaining ring of the assembly in FIG. 19;
FIG. 21 is a perspective view of the ball and socket fastener with the anchoring member illustrating the cooperation between the spherical ball and the connector member;
FIG. 22 is a perspective view of retaining rings illustrating the interaction between the two retaining rings when the assembly is in the locked position illustrated in FIG. 21;
FIG. 23 is a perspective view of the ball and socket fastener with the anchoring member illustrating the polyaxial cooperation between the spherical ball and the U-shaped connector member in an unlocked position;
FIG. 24 is a perspective view of the grooves which accommodate the retaining rings shown in FIG. 22;
FIG. 25 is a perspective view of the retaining rings shown in FIG. 22 illustrating the interaction between the two retaining rings when the assembly is in an unlocked position, illustrated in FIG. 23.

DETAILED DESCRIPTION OF THE PREFERRED EMBODIMENT

Figure 1:
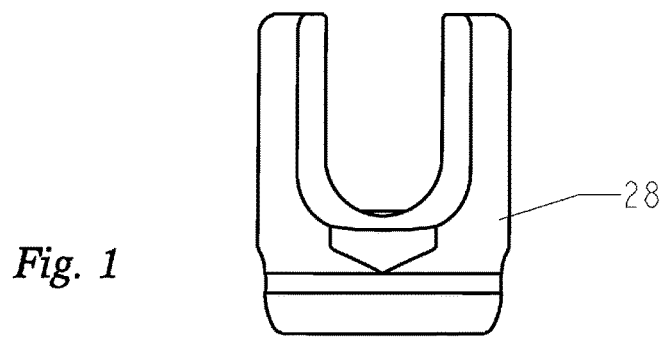
FIG. 1 is aside view of the U-shaped connector.

While the present invention is susceptible of embodiments in various forms, there is shown in the drawings and will hereinafter be described a presently preferred embodiment with the understanding that the present disclosure is to be considered an exemplification of the invention and is not intended to limit the invention to the specific embodiments illustrated.

The terminology used herein is for the purpose of describing particular embodiments only and is not intended to be limiting of the invention.

Definitions

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end farther from the device operator during use.

Device

What is needed in the art, and this invention provides, is a polyaxial ball and socket joint that can be adapted for use in a spinal fixation system that includes the advantages of known devices, while addressing the shortcomings that they exhibit. The system should allow component interchangeability at point of installation, thereby addressing a wide variety of spinal deformities with less components. In addition, the system should allow the stabilized angular placement position of the connector components during installation.

Referring generally to the Figures, disclosed is an exemplary embodiment of the polyaxial ball and socket fastening system adapted for use in a spinal fixation system. The fastening system includes a spherical ball connector (18) secured or formed integrally with a bone anchor (12) and connecting assembly that includes a snap-in type receptacle for the spherical ball connector (18) to form a polyaxial joint allowing a range of motion (ROM). The connector assembly (28) also includes a receiver that may be used in conjunction with a connecting rod member (70) for securing at least two bone anchors (12) together.

The bone anchor (12) of the preferred embodiment is a bone anchor (12) including a shank (14) having a length with at least one helical thread (16) formed along the length thereof. It is important to note that the proportions of the bone anchor (12) depicted are for illustrative purposes only and variations in the length of the shank, diameter of the screw, thread pitch, thread length, number of thread leads, shank induced compression and the like may be varied without departing from the scope of the invention. At the upper or proximal end (20) of the shank (14) is a ball shaped spherical ball connector (18) having a predetermined diameter. A driver receptacle (22), which may be configured as a plurality of recesses or a single recess for an insertable driver tool, is located along the upper portion (19) of the spherical ball connector (18) for use in installing the bone anchor (12) by use of a driving tool. It should be noted that the driver receptacle (22) may be any shape, male or female, suitable for cooperation with a driving tool to rotate the bone anchor (12) into its final position.

As illustrated in FIGS. 2, 17, 19, 21 and 23, a U-shaped connector assembly (28) is illustrated having a first retaining ring (40), a blocking ring (40a) and a second retaining ring (40b) that is insertable into a first (30), a second (30a) and second retaining ring groove (30b) respectively. The first retaining ring (40) and second retaining ring (40b) are split retaining rings, the blocking ring (40a) is a split ring shaped and sized to snap over the circumference of the second split retaining ring (40b) when the spherical ball connector is pushed upwards. The blocking ring (40a) holds the second split retaining ring (40b) in place by pinching (interference fit) an outer diameter of the second split retaining ring (40b) with an inner diameter of the blocking ring (40). The blocking ring (40a) increases the width of the cross section as compared with the ring "40a" set forth in U.S. Pat. No. 9,615,858. The blocker ring (40a) of the instant invention provides nearly 360 degrees of coverage for the second ring (40b), the only coverage not provided is at the split. The retaining and blocking rings (40, 40a, 40b), shown in greater detail in FIGS. 5, 8, 9, 22 and 25, are made of a biocompatible spring temper material which may include shape memory alloys and in a preferred embodiment is stainless steel.

Figure 29:
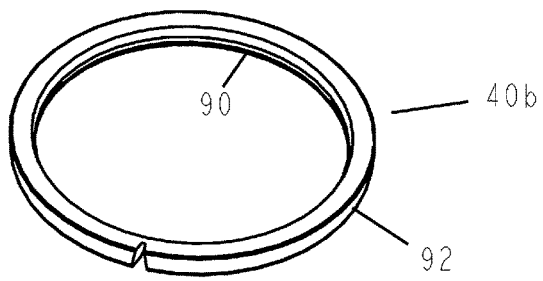
FIG. 29 is a perspective view of the second split retainer ring in a continuous inner side wall position.
Figure 30:
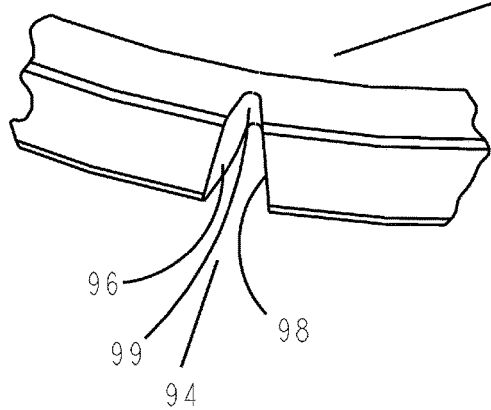
FIG. 30 is an enlarged view of a portion of the split ring illustrated in FIG. 29.
Figure 31:
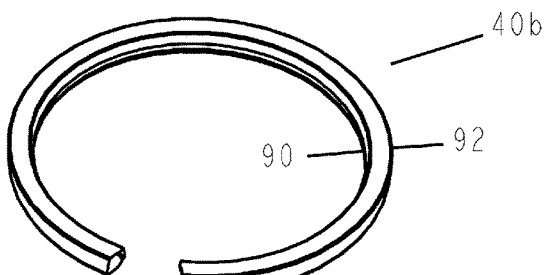
FIG. 31 is a perspective view of the second split retainer ring in a detached position.
Figure 32:
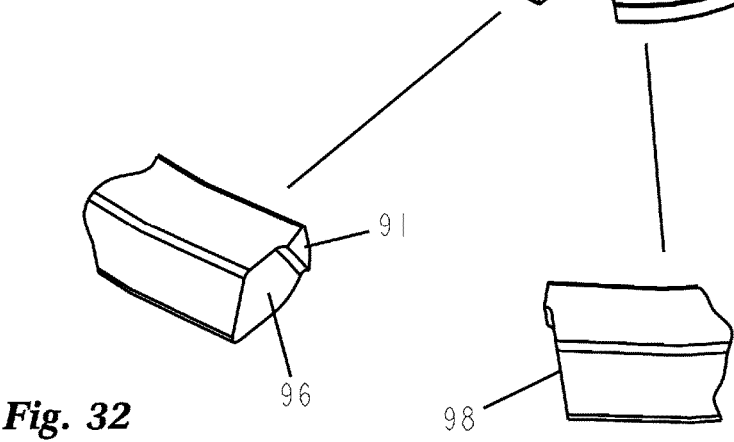
FIG. 32 is an enlarged view of a portion of the split ring illustrated in FIG. 31.

Referring to FIGS. 29-30, set forth is a preferred embodiment of the second split retaining ring (40b). The second split retaining ring (40b) is further defined by a 360 degree continuous inner surface wall (90) and an outer surface wall (92) with an angular shaped notch (94). The notch (94) having a first angular shaped wall (96) adjoining a second angular shaped wall (98) by an end wall (99). In the preferred embodiment the second split retaining ring (40b) is formed by a continuous inner surface wall (90) sized for receipt of the spherical head of a pedicle screw during installation. When the spherical head of a pedicle screw is forced through the continuous inner surface wall (90) the ring (40b) fractures at the notch (94) to create the split ring as illustrated in FIG. 31. The notch (94) is constructed and arranged to split when a predetermined force is applied to the continuous inner surface wall (90) resulting in a tactile feel and an audible sound. The tactile feel can be felt at the moment of the notch break, and the snap of the ring material provides a sound that can be clearly heard during the installation step. The tactile feel and audible sound provide a surgeon with positive reinforcement that the split retainer ring has been pressed against the spherical head of the screw with sufficient force to cause the spherical head to pass the second split retainer ring (40b). To further allow for aligning the second split retainer ring (40b) the upper edge (91) of the inner surface wall (90) is chamfered to meet the outer surface of a spherical ball.

Figures 12, 13:
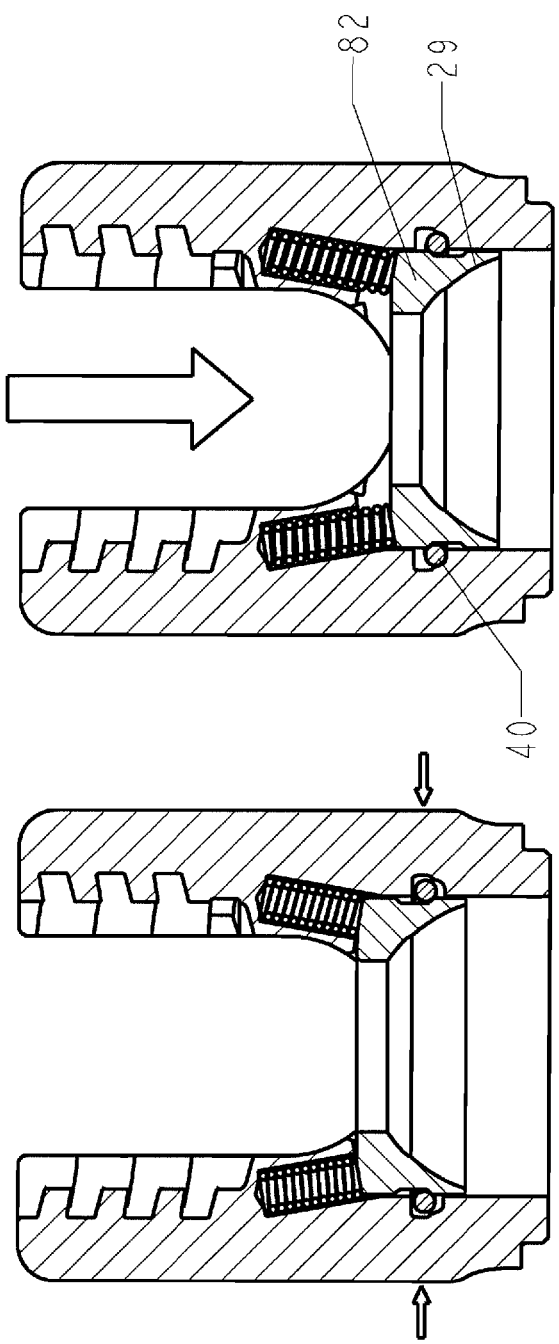
Figure 26:
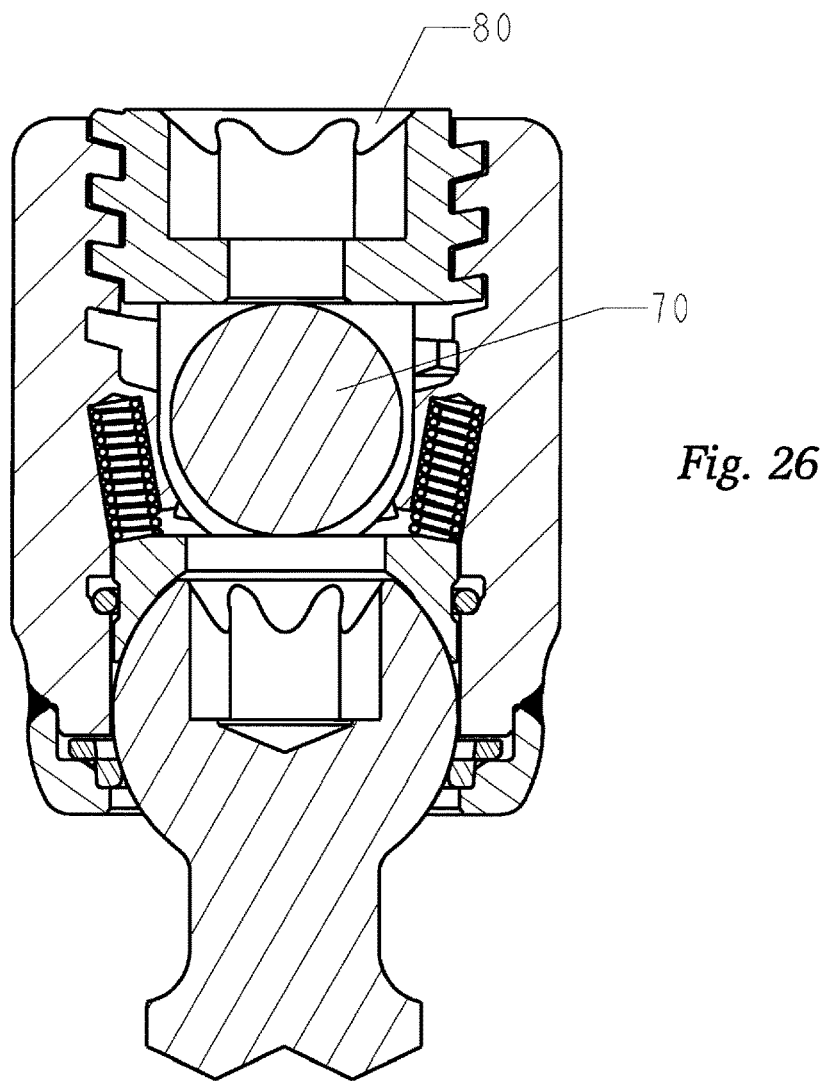
FIG. 26 is a perspective view of a set screw.
Figure 27:
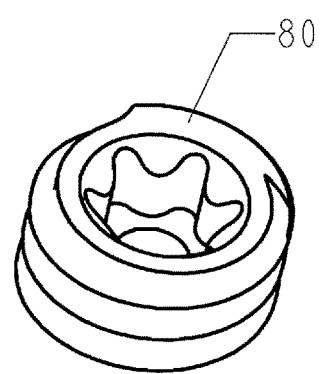
FIG. 27 is a plane view of the assembled ball and socket fastener.

In some embodiments, the U-shaped connector assembly comprises at first retaining ring (40), preferably a split retaining ring. This is illustrated in FIGS. 10 through 13. As the anchor cap (82) of the U-shaped connector assembly is pushed upwards during the capture of the spherical ball connector (18) (not shown), the first retaining ring (40) expands and slides up the side wall (36) to a displaced position at the second annulus (37). Once past the greatest diameter of the spherical ball connector (18) the first retaining ring (40) will contract and slide back down the side wall (36) from its displaced position at the second annulus (37) to its normal position along the lower end wall (34) as illustrated in FIG. 12. The spacing of the first split retaining ring (40) within the split ring groove (30) and the material of the first split retaining ring (40) provides a biasing force that ensures that the first split retaining ring (40) will not bend as the spherical ball connector (18) passes the first split retaining ring (40). After the spherical ball connector (18) has been captured by the first split retaining ring (40), the first split retaining ring (40) will thereafter serve to maintain a slight upward force on the spherical ball connector (18) as the first split retaining ring (40) attempts to contract to a diameter smaller than the diameter (D1) of the first annulus (35). The upward biasing force created by the first split retaining ring (40) creates a frictional engagement of the spherical ball connector (18) with the lower end wall (34) and the side wall (36) and the lower portion (17) of the spherical ball connector (18) as illustrated in FIG. 13. The split retaining ring provides a tactile feel wherein the retainer clip snaps into position to indicate proper installation. The retaining ring can also comprise a pressure ring (40') and a first split retaining ring (40) wherein the pressure ring (40') in this embodiment is shown as having a pentagonal shape. The pressure ring captures the split retaining during the capture of a spherical ball connector as described above. The assembly is shown in FIGS. 14 and 15.

Figure 2:
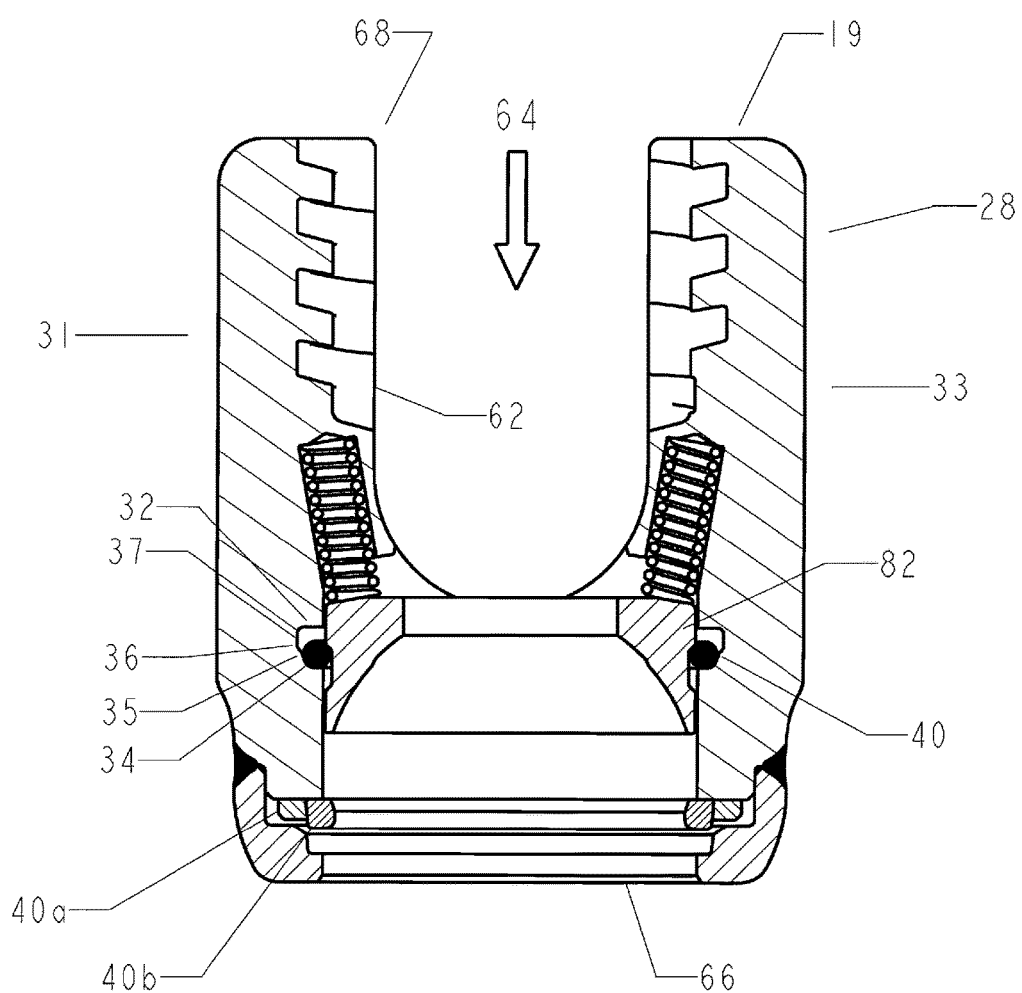
FIG. 2 is a cross sectional view of the U-shaped connector and anchor cap.
Figures 10, 11:
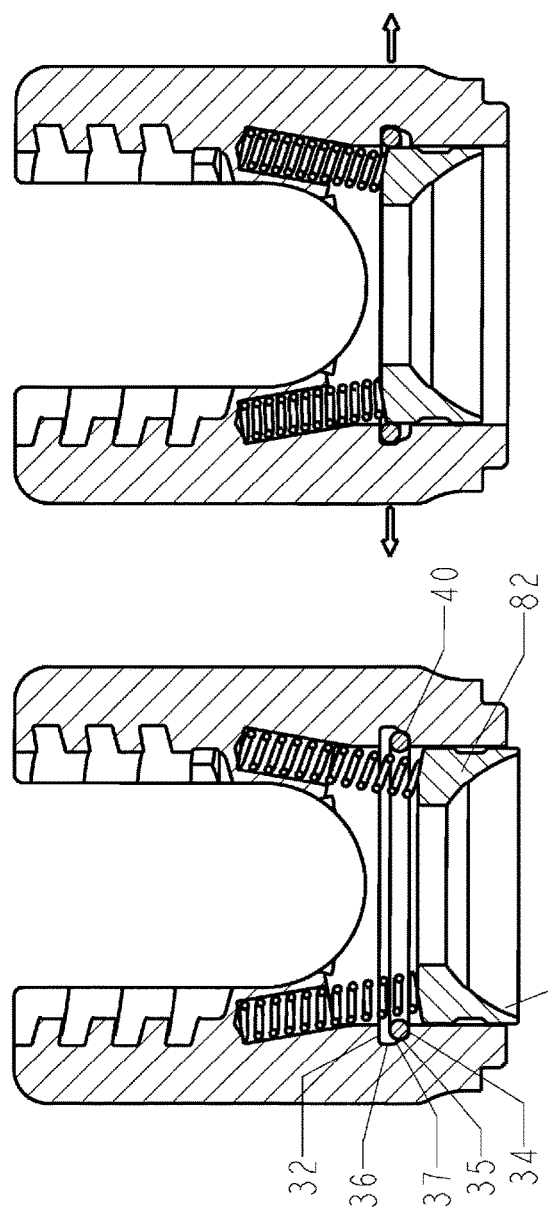
FIGS. 10 to 13 are cross-sectional views of the U-shaped connector illustrating the insertion of the anchor cap.

As illustrated in FIGS. 2, 21 and 23. The U-shaped connector assembly (28) includes an internal passageway (64) that extends from a first or distal end (66) to a second or proximal end (68). The diameter of the internal passageway (64) being greater than the diameter of the spherical ball connector (18) at said first end (66) and the diameter of the internal passageway (64) at said second end (68) being smaller than the diameter of the spherical ball connector (18). The U-shaped connector assembly (28) includes a base with a pair of U-shaped openings forming a first upstanding side wall (31) and second side wall (33).

Shown in FIG. 21, the first retaining ring groove (30) is further defined by upper end wall (32), a lower end wall (34) and a side wall (36) therebetween. The side wall (36) is angularly positioned wherein the junction of the lower end wall (34) and side wall (36) forms a first annulus (35) having a first diameter (D1) and the junction of the upper end wall (32) and side wall (36) forms a second annulus (37) with a second diameter (D2), larger than the first diameter (D1).

Shown in FIGS. 21 and 23, the blocking ring groove (30a) is further defined by upper end wall (32a), a lower end wall (34a) and a side wall (36a) therebetween. The side wall (36a) can be vertically or angularly positioned wherein the junction of the lower end wall (34a) and side wall (36a) forms a first annulus (35a) having a first diameter (D1a) and the junction of the upper end wall (32a) and side wall (36a) forms a second annulus (37a) with a second diameter (D2a). The second diameter (D2a) is larger than the first diameter (D1a) when the side wall (36a) is angularly positioned.

Shown in FIGS. 21 and 23, the second retaining ring groove (30b) is further defined by upper end wall (32b), a lower end wall (34b) and a side wall (36b) therebetween. The side wall (36b) can be vertically or angularly positioned wherein the junction of the lower end wall (34b) and side wall (36b) forms a first annulus (35b) having a first diameter (D1b) and the junction of the upper end wall (32b) and side wall (36b) forms a second annulus (37b) with a second diameter (D2b). The second diameter (D2a) is larger than the first diameter (D1a) when the side wall (36b) is angularly positioned.

In embodiments, the diameter (D1a) of the first annulus (35a) and the diameter (D2a) of the second annulus (37a) of the second groove (30a) is greater than (i) the diameter (D1b) of the first annulus (35b) and (ii) the diameter (D2b) of the second annulus (37b) of the second groove (30b). In such an embodiment, the blocking ring (40a) is larger in diameter than the second retaining ring (40b) wherein the second split retaining ring (40b) is positioned around the blocking ring (40a) when the spherical ball connector is pushed upwards so that the second groove (30a) now contains the blocking ring (40a) and second split retaining ring (40b) which have expanded to tightly fit into the second groove (30a).

In assembly, the shank (14) of the bone anchor (12) is inserted into the pedicle of a patient by use of a driving tool (not shown), fixing the position of the bone anchor (12). The U-shaped connector assembly (28) can then be attached over the spherical ball connector (18) of the bone anchor (12), wherein the spherical ball connector (18) engages the retaining and blocking rings (40, 40a, 40b). FIG. 23 is a cross sectional view of the spherical ball connector (18) in the process of assembly to the socket of the U-shaped connector assembly (28) by placement against the retaining and blocking rings (40, 40a, 40b). Referring now to FIG. 21, as the U-shaped connector (28) contacts the spherical ball connector (18), the blocker ring and second split ring (40a, 40b), positioned in split ring grooves (30a, 30b), contact the spherical ball connector (18) and are moved from their normal positions along the lower end walls (34a, 34b) to a position along the upper end walls (32a, 32b) respectively. At the widest point of the spherical ball connector (18) contacts the second split retaining ring (40b), the second split retaining ring (40b) expands in diameter along the upper end wall (32b) approaching the second annulus (37b). In this position the second split retaining ring (40b) is able to expand up to the diameter of the blocking ring (40a) which expands into the diameter (D2a) presented by the second annulus (37a) allowing the second split retaining ring (40b) to pass the spherical ball connector (18) which allows the U-shaped connector (28) to engage the spherical ball connector (18). The blocking ring (40a) exerts an inward force against the second split retaining ring (40b) so that the spherical ball connector is held in position as the upward biasing force created by the blocking ring and second retaining rings (40a, 40b) creates a frictional engagement of the spherical ball connector (18) with the lower end wall (34a) and the side wall (36a) and the lower portion (17a) of the spherical ball connector (18).

In some embodiments the first retaining ring (40), is a split retaining ring. In assembly, once this first retaining ring (40) is past the spherical ball connector (18), the first split retaining ring (40) will contract and slide back down the side wall (36) from its displaced position at the second annulus (37) to its normal position along the lower end wall (34), returning to diameter (D1). In this position the first split retaining ring (40) prohibits the spherical ball connector (18) from removal, as shown in FIG. 21. The more pressure that is applied in a removal attempt, the more resistance is provided by the first split retaining ring (40) as it is frictionally engaged between the spherical ball connector (18), the lower end wall (34), and the sidewall (36).

The spacing of the first split retaining ring (40) within the split ring groove (30) and the material of the first split retaining ring (40) provides a biasing force that ensures that the first split retaining ring (40) will not bend as the spherical ball connector (18) passes the first split retaining ring (40). After the spherical ball connector (18) has been captured by the first split retaining ring (40), the first split retaining ring (40) will thereafter serve to maintain a slight upward force on the spherical ball connector (18) as the first split retaining ring (40) attempts to contract to a diameter smaller than the diameter (D1) of the first annulus (35). The upward biasing force created by the first split retaining ring (40) creates a frictional engagement of the spherical ball connector (18) with the lower end wall (34) and the side wall (36) and the lower portion (17) of the spherical ball connector (18). The split retaining ring provides a tactile feel wherein the retainer clip snaps into position to indicate proper installation.

The anchor cap (82) comprises a first retaining ring (40), which is used to provide additional stability to the connector assembly during and after insertion into the bone of a patient. The anchor cap (82) has a spherical surface formed on a lower end (84) which provides a seat for the spherical ball connector (18), and can be inserted into the internal passageway of the U-shaped connector assembly (28) to engage with the first retaining ring (40) in a first split ring groove (30). The anchor cap (82) seats with and is resiliently biased against an upper portion (19) of the spherical ball connector (18) and engages the spherical ball connector (18) so as to keep the U-shaped connector assembly (28) in position during installation. The anchor cap (82) comprises at least one compressible or non-compressible member (100) which extends from the top of the anchor cap in an upward direction distal to the anchor cap (82) and into a cavity (101) in the U-shaped connector assembly (28). An example of a compressible member is a spring. An example of a non-compressible member is a screw. Of course, whether a member is compressible or non-compressible will also depend on the composition of the member, e.g., metal, rubber etc. FIGS. 21 and 23 are cross-sectional views of an anchor cap (82). As illustrated in FIGS. 21 and 23, the anchor cap (82) is predominantly cylindrical having an outer surface including an anchor cap groove (30) for engagement with a first retaining ring (40) located in a first ring groove (30) on the inner side surface (29) of the U-shaped connector and the outer surface (102) of the anchor cap (82). The anchor cap (82) has a lower end (84) which is predominantly spherical to engage with and provide a seat for the spherical ball connector (18). As illustrated in FIGS. 21 and 23, as the anchor cap (82), which, is inserted through the bottom of the connector assembly (28) prior to connecting the connector assembly (28) to a bone anchor (12), the first retaining ring (40) moves from its initial position along an upper wall of the first ring groove (30) moving up and expanding outward along a side wall of the first retaining ring groove (32) to a lower wall of the first retaining ring groove (34) and then a lower annulus of the first retaining ring groove (34) to allow the anchor cap (82) to pass. When the anchor cap groove (83) and the first retaining ring groove (30) are in alignment, the first retaining ring (40) will expand, thereby, mechanically connecting the anchor cap (82) to the connector assembly (28). The expansion of the first retaining ring (40) provides a biasing upward force on the anchor cap (82) because of the angled slope of the anchor cap groove (83). In preferred embodiments, the first retaining ring is a split retaining ring.

A bone anchor (14) can be inserted into the connector assembly (28) from the bottom. As the bone anchor (14) is inserted, the first split retaining ring (40) moves in the split ring groove (30) as described above to allow the connector assembly (28) to engage the spherical ball connector (18). As the spherical ball connector (18) passes the first split retaining ring (40), the upper portion (19) of the spherical ball connector (18) comes into contact and seats with the lower end (84) of the anchor cap (82). The first split retaining ring (40) prevents the anchor cap (82) from disengaging with the connector assembly (28).

Illustrated in FIGS. 21 and 23, the seating of the spherical ball connector (18) with the anchor cap (82) creates a frictional engagement between the upper portion (19) of the spherical ball connector (18) and the lower end (83) of the anchor cap (82) caused by the downward force of the anchor cap (82) on the spherical ball connector (18) from the contraction of the retaining and blocking rings (40, 40a, 40b). This frictional engagement between the two surfaces allows the connector assembly (28) to be positioned and maintained at different angles for installation of a connecting rod member (70).

After the anchor cap (82) and spherical ball connector (18) have been inserted into the connector assembly (28), a connecting rod member (70) and set screw (80) can be inserted to lock the connector assembly (28) together. The set screw (80) exerts a force on the connecting rod member (70) which in turn exerts a force on the anchor cap (82), increasing the frictional connection between the anchor cap (82) and the spherical ball connector (18). In this configuration, the spherical ball connector (18) is held more stable by the greater contact surface than without the anchor cap (82) and only the point contact of the connecting rod member (70) on the upper portion (19) of the spherical ball connector (18).

Figure 28:
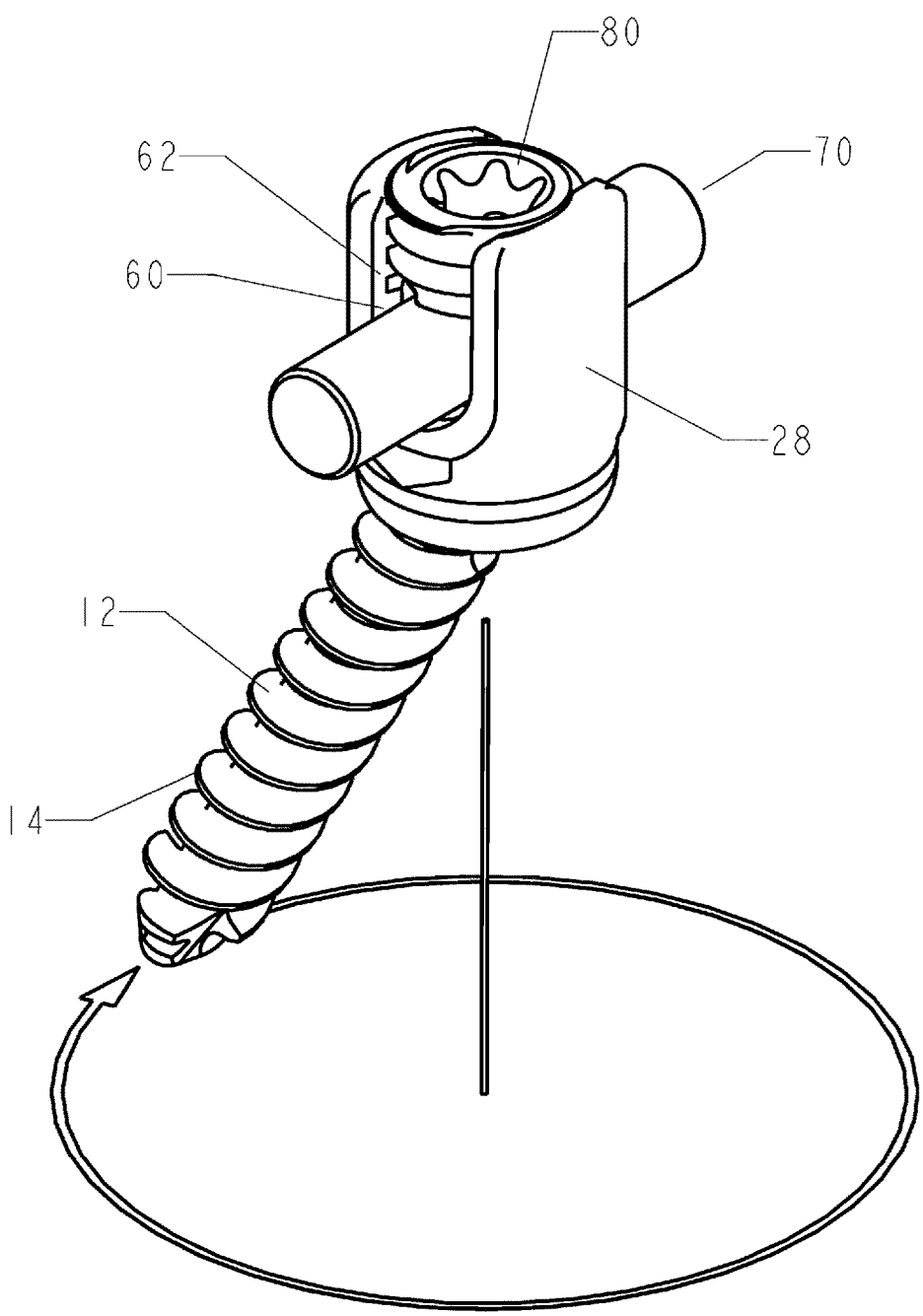
FIG. 28 is a perspective view of the ball and socket fastener with the anchoring member illustrating the polyaxial cooperation between the spherical ball and the connector member.

As illustrated in FIG. 28, once mounted the polyaxial action of the U-shaped connector assembly (28) allows for ease of positioning a connecting rod member (70) into the U-shaped receptacle opening (60). A securing element in the form of a set screw (80) is inserted into the threaded portion (62) of the U-shaped connector assembly (28) until the set screw (80) contacts the connecting rod member (70), causing the connecting rod member (70) to press against the spherical ball connector (18). The insertion of the securing element causes the spherical ball connector (18) to wedge the lower portion (17) of the spherical ball connector (18) against the first split retaining ring (40) thereby securing the assembly in a desired position. The inner side surface (29) of the anchor cap (82) is generally spherical and constructed and arranged in configuration to be complimentary to the spherical surface on the spherical ball connector (18). It should be appreciated that this construction provides a three point contact between the U-shaped connector assembly (28) and the spherical ball connector (18) by capturing the connector rod member (70) therebetween with the set screw (80) allowing for securement.

The set screw (80) can have various socket forms for a driver receptacle, for example, a hex socket, a hexalobular (star shaped) socket, and the like. The socket shape of the set screw (80) is not limited to these two known patterns and can include others such as a square/Robertson type socket, pentagon socket, slotted socket, any of the cruciform socket types, TTAP socket type, or any other socket type which would allow the screw to be securely tightened.

Unique to this invention is the ability for the surgeon to attach various types of bone anchors or the like to the connecting assembly, after having installed the bone anchor into the bone of a patient. While there are a myriad of anchoring devices that can be adapted to include the spherical ball, bone hooks etc., for ease of illustration the bone screw is depicted and it is well known that various lengths and diameters of bone screws are available, many of which would not fit through the inner diameter of the connector assembly. Thread styles, lengths and so forth that are best suited for installation may be estimated before surgery but it is well known that only during actual surgery can the proper style be confirmed. Because it is most difficult to predict the proper combination of anchor screw and connector member, surgeons must either have a large selection of spinal implants to choose from or be forced to use the closest combination and hope that it will suffice.

In embodiments, multiple bone anchor (12) sizes can be accommodated by a single connector assembly (28).

It should be noted that while various types of bone screws have been mentioned, the instant installation allows placement of an anchoring device having a spherical connector into position before a connector member is attached. This provides the surgeon with an option of positioning the bone screw before placement of the connecting member thereby providing a simplified installation should positioning of the anchoring screw be difficult due to muscle or other interference. Installation of a bone screw with the connecting member allows a range of mobility as well as better visual positioning. Further, while the U-shaped connector member is depicted, various types of connector members may be used in combination with the spherical ball connector (18) allowing a surgeon to select the appropriate combination during surgery thereby enhancing the success for the benefit of the patient as well as lowering cost of inventory necessary when estimating the various types of situations that the surgeon may encounter during the operation.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A bottom loading connector assembly for polyaxial coupling to an anchored bone screw having a spherical ball with a shank having at least one thread formed along a length of the shank, comprising:
   a connector assembly having a first side wall and a second side wall forming a U-shaped opening, a top end and a bottom end with a passageway therebetween having a diameter along the bottom end being greater than a major diameter of a bone screw spherical ball and a diameter along the top end being smaller than the major diameter of the spherical ball;
   a first groove formed along a lower end of said passageway;
   a retaining ring positionable in said first groove, said retaining ring having a continuous inner surface wall and a notch formed in an outer surface wall;
   a second groove juxtapositioned to said first groove;
   a blocker split ring positionable in said second groove;
   an anchor cap dimensioned to fit over a portion of the spherical ball;
   and a set screw releasably securable to the top end of said connector assembly;
   wherein said bottom end of said connector assembly is positioned over the spherical ball of the anchored bone screw, said retaining ring and said blocker split ring expands to permit passage of the spherical ball whereby said blocker split ring captures said retaining ring maintaining said retaining ring in position beneath the spherical ball thereby reducing the diameter of the passageway and preventing removal of said connector assembly from said anchored bone screw; wherein said retaining ring expands at said notch and snaps into said blocker split ring when said spherical ball moves past said retaining ring in an expanded state, wherein said blocker split ring applied pressure around a circumference of said retaining ring to assist in positioning said retaining ring along a lower surface of said spherical ball.

2. The bottom loading connector assembly for a polyaxial screw as set forth in claim 1, wherein said blocker split ring is shaped and sized to snap over said retaining ring providing about 360 degree coverage.

3. The bottom loading connector assembly for a polyaxial screw set forth in claim 1, wherein said retaining ring is constructed and arranged to indicate a change in diameter by tactile feel and sound when the retaining ring is positioned over the spherical ball of the anchored bone screw.

4. The bottom loading connector assembly for a polyaxial screw as set forth in claim 1, wherein a first junction is formed by a side wall of the second groove and a lower end of the second groove, the first junction having a first diameter, and a second junction formed by the side wall of the second groove and an upper wall of the second groove, the second junction having a second diameter.

5. The bottom loading connector assembly for a polyaxial screw as set forth in claim 4, wherein said second diameter of said second junction is greater than said first diameter of the first junction.

6. The bottom loading connector assembly for a polyaxial screw as set forth in claim 4, wherein said retaining ring can expand in diameter within said second groove up to the second diameter of the second annulus as the spherical connector is moved past said retaining ring.

7. The bottom loading connector assembly for a polyaxial screw as set forth in claim 1, wherein an internal passageway at said top end of said connector assembly has a generally spherical surface and is constructed and arranged in configuration to be complimentary to said spherical surface of said spherical connector.

* * * * *